United States Patent [19]

Nakai et al.

[11] Patent Number: 5,284,919
[45] Date of Patent: Feb. 8, 1994

[54] RESIN COMPOSITIONS AND A METHOD OF CURING THE SAME

[75] Inventors: Noboru Nakai, Hiratsuka; Osamu Isozaki, Yokohama; Naozumi Iwasawa, Hiratsuka, all of Japan

[73] Assignee: Kansai Paint Company, Limited, Amagasaki, Japan

[21] Appl. No.: 672,792

[22] Filed: Mar. 21, 1991

Related U.S. Application Data

[62] Division of Ser. No. 402,408, Sep. 5, 1989, Pat. No. 5,026,793.

[30] Foreign Application Priority Data

Sep. 9, 1988 [JP] Japan .................... 63-227093

[51] Int. Cl.$^5$ ............................. C08G 77/04
[52] U.S. Cl. ......................... 525/195; 525/208; 525/209
[58] Field of Search .............. 525/208, 209, 195

[56] References Cited

U.S. PATENT DOCUMENTS 4,772,672  9/1988  Isozaki et al. .................. 526/273
4,818,790  4/1989  Ooka et al. ..................... 525/103

FOREIGN PATENT DOCUMENTS 56-160054  9/1981  Japan .

OTHER PUBLICATIONS

Patent Abstracts of Japan, vol. 6, No. 42 (E-98)(920), Mar. 16, 1982.

Primary Examiner—Melvyn I. Marquis
Assistant Examiner—D. Aylward
Attorney, Agent, or Firm—Armstrong, Westerman, Hattori, McLeland & Naughton

[57] ABSTRACT

A resin composition comprising two different compounds, A and B, with a number average molecular weight of 3,000 to 200,000 and a chelate compound. Compound A has two or more hydroxyl groups. Compound B has two or more epoxy groups and one or more of the following silane groups silanol, alkoxy silane and acyloxy silane.

2 Claims, No Drawings

RESIN COMPOSITIONS AND A METHOD OF CURING THE SAME

This is a division of application Ser. No. 402,408 filed Sep. 5, 1989. U.S. Pat. No. 5,026,793 issued Jun. 25, 1991.

The present invention relates to novel resin compositions and a method of curing the same.

For the curing of resins containing hydroxyl groups as functional groups, methods employing diisocyanate compounds, melamine resin, etc. have heretofore been employed. However, with diisocyanates, the resulting films are generally inadequate in weather resistance and tend to undergo yellowing. Furthermore, the resin compositions have short pot lives, not to speak of the toxicity problem associated with diisocyanates.

When a melamine resin is employed, a high baking temperature over about 140° C. is necessary and the resulting film is not as resistant to acid as desired.

It is an object of the present invention to provide novel hydroxyl group-containing resin compositions which are curable at a sufficiently high rate at a low temperature not exceeding 100° C. and a method of curing the same compositions.

It is another object of the invention to provide novel hydroxyl group-containing resin compositions which are not only having good curability at low temperature but adapted to yield a cured film having excellent weather resistance, acid resistance and other physical properties and a method of curing the same compositions.

Other objects and advantages of the present invention will become apparent as the following description of the invention proceeds.

The present invention provides novel resin compositions and a method for curing the same, all of which are described hereinafter and summarized immediately below.

(1) A resin composition comprising (A) a high molecular weight hydroxy compound containing an average of two or more hydroxyl groups per molecule and having a number average molecular weight of 3,000 to 200,000, (B) an epoxy compound containing an average of two or more epoxy groups per molecule and having a number average molecular weight of 120 to 200,000, (C) a silane compound containing an average of one or more functional groups selected from the class consisting of alkoxysilane, silanol and acyloxysilane groups per molecule and having a number average molecular weight of 104 to 200,000, and (D) at least one metal chelate compound selected from the class consisting of aluminum chelate compounds, titanium chelate compounds and zirconium chelate compounds (hereinafter referred to as Invention I);

(2) a resin composition which comprises (A) said high molecular weight hydroxy compound, (E) a high molecular weight compound containing an average of two or more epoxy groups per molecule and an average of one or more functional groups selected from the class consisting of alkoxysilane, silanol and acyloxysilane groups per molecule and having a number average molecular weight of 3,000 to 200,000, and (D) said metal chelate compound (hereinafter referred to as Invention II);

(3) a resin composition which comprises (F) a high molecular weight compound containing an average of two or more hydroxyl groups and an average of one or more functional groups selected from the class consisting of alkoxysilane, silanol and acyloxysilane groups per molecule and having a number average molecular weight of 3,000 to 200,000, (G) a low molecular weight compound containing an average of two or more epoxy groups per molecule and having a number average molecular weight of 240 to 5,000, and (D) said metal chelate compound (hereinafter referred to as Invention III);

(4) a resin composition which comprises (H) a high molecular weight compound containing an average of two or more hydroxyl groups and an average of two or more epoxy groups per molecule and having a number average molecular weight of 3,000 to 200,000, (C) said silane compound, and (D) said metal chelate compound (hereinafter referred to as Invention IV); and (5) a method of curing a resin composition which comprises crosslinking any of the resin compositions of Invention I through IV at a temperature not exceeding 100° C.

To overcome the aforementioned disadvantages of the prior art technologies, the inventor of the present invention did assiduous and diligent studies for developing a hydroxyl group-containing resin composition which is curable at low temperature to yield satisfactory film properties. As a result, it was found that a high molecular weight compound containing two or more hydroxyl groups per molecule may be caused to cure at a sufficiently high rate even at a low temperature not exceeding 100° C. when it is so arranged that the curing reaction may take place in the presence of functional groups of at least one selected from the class consisting of alkoxysilane, silanol and acyloxysilane groups as well as epoxy groups with the aid of, as a curing catalyst, at least one metal chelate compound selected from the class consisting of aluminum chelate compounds, titanium chelate compounds and zirconium chelate compounds and that the resulting cured film has excellent weather resistance, acid resistance and other physical properties.

The present invention is predicated on the above findings.

The high molecular weight hydroxy compound (A) to be used in Invention I is a compound containing an average of two or more hydroxyl groups per molecule and has a number average molecular weight of 3,000 to 200,000, preferably 5,000 to 80,000. If the number of hydroxyl groups is less than 2 on the average per molecule, the curing performance and the gel fraction ratio of the film will be decreased. From the standpoint of weatherability and water resistance, the number of hydroxyl groups is preferably not more than 400 on the average per molecule. If the number average molecular weight of compound (A) is less than 3,000, the impact resistance, weatherability and other physical properties will not be as good as desired. On the other hand, if the number average molecular weight exceeds 200,000, the compatibility of the compound with the other components will be poor so that the uniformity of cure will be sacrificed to detract from the weather resistance of the cured film.

As examples of the high molecular weight hydroxy compound (A), compounds in the following categories (1) through (6) can be mentioned.

(1) High molecular weight acrylic polyol compounds: Homopolymers of hydroxyl group-containing vinyl monomers (I) (for example, hydroxy-$C_{2-8}$ alkyl esters of (meth)acrylic acid such as hydroxyethyl (meth)acrylate, hydroxypropyl (meth)acrylate, etc. and adducts of such hydroxy-$C_{2-8}$ alkyl esters of (meth)acrylic acid with lactones such as e-caprolactone, Υ-valerolactone, etc.) and copolymers of said hydroxyl group-containing vinyl monomers (I) with other $\alpha,\beta$-ethylenically unsaturated monomers (II).

Examples of said $\alpha,\beta$-ethylenically unsaturated monomers (II) include:

(a) Esters of acrylic acid or methacrylic acid: $C_{1-18}$ alkyl esters such as methyl acrylate, ethyl acrylate, propyl acrylate, isopropyl acrylate, butyl acrylate, hexyl acrylate, octyl acrylate, lauryl acrylate, methyl methacrylate, ethyl methacrylate, propyl methacrylate, isopropyl methacrylate, butyl methacrylate, hexyl methacrylate, octyl methacrylate, lauryl methacrylate; $C_{2-18}$ alkoxyalkyl esters such as methoxybutyl acrylate, methoxybutyl methacrylate, methoxyethyl acrylate, methoxyethyl methacrylate, ethoxybutyl acrylate, ethoxybutyl methacrylate, etc.; $C_{2-8}$ alkenyl esters such as allyl acrylate, allyl methacrylate, etc.; $C_{3-18}$ alkenyloxyalkyl esters such as allyloxyethyl acrylate, allyloxyethyl methacrylate and so on.

(b) Vinyl-aromatic compounds: styrene, $\alpha$-methylstyrene, vinyltoluene, p-chlorostyrene and the like.

(c) Polyolefin compounds: butadiene, isoprene, chloroprene and so on.

(d) Others: acrylonitrile, methacrylonitrile, methyl isopropenyl ketone, vinyl acetate, VeoVa monomers (Shell Chemical), vinyl propionate, vinyl pivalate, acrylic acid, methacrylic acid and so on.

(2) High molecular weight polyester polyol compounds: The compounds obtainable by esterifying polybasic acids (compounds containing 2 to 4 carboxyl groups per molecule, such as phthalic acid, isophthalic acid, terephthalic acid, maleic acid, pyromellitic acid and the corresponding anhydrides) with polyhydric alcohols (alcohols containing 2 to 6 hydroxyl groups in the molecule, such as ethylene glycol, polyethylene glycol, propylene glycol, neopentyl glycol, 1,6-hexanediol, trimethylolpropane, pentaerythritol, glycerol, tricyclodecanedimethanol, etc.). Aside from the above compounds, monobasic acids (for example, fatty acids such as castor oil fatty acid, soybean oil fatty acid, tall oil fatty acid, linseed oil fatty acid, etc., benzoic acid and so on) can also be used if necessary.

(3) High molecular weight fluorine-containing polyol compounds: Copolymers of fluorine-containing (meth)acrylate monomers (III) (for example, perfluorooctylethyl (meth)acrylate, perfluoroisononylethyl (meth)acrylate, etc.) with monomers (I); copolymers of monomers (I), (II) and (III); copolymers of fluorinecontaining ethylene monomers with vinyl ethers (for example, copolymer of monochlorotrifluoroethylene, alkylvinyl ether and hydroxyalkylvinyl ether [Lumiflon, trademark of Asahi Glass Co., Ltd.])

(4) High molecular weight polyurethane polyol compounds: Isocyanate-free polymers obtainable by modifying said high molecular weight acrylic polyol compounds, polyester polyol compounds, etc. with polyisocyanates (for example, tolylene diisocyanate, xylene diisocyanate, hexamethylene diisocyanate, isophorone diisocyanate, etc.)

(5) High molecular weight silicone polyol compounds: Alkoxysilane-, acyloxysilane- or silanol-free polymers obtainable by modifying said high molecular weight acrylic polyol compounds, polyester polyol compounds, etc. with silicone resins (for example, Z-6018 and Z-6188 [both are products of Dow Corning], SH5050, SH6018 and SH6188 [all are products of Toray Silicone])

(6) Vinyl alcohol-styrene copolymers.

The epoxy compound (B) mentioned hereinbefore contains an average of 2 or more epoxy groups per molecule and has a number average molecular weight of 120 to 200,000, preferably 240 to 80,000. If the number of epoxy groups is less than 2, the curing performance and gel fraction ratio will be decreased. From the standpoint of curing performance, the average number of epoxy groups is preferably not more than 500 per molecule. Epoxy compounds with number average molecular weights less than 120 are hardly available. On the other hand, if the number average molecular weight exceeds 200,000 the compatibility of the compound with the other components is poor so that the weatherability of the cured film is sacrificed.

From the standpoint of curing performance, the epoxy compound (B) preferably has alicyclic epoxy groups. As specific examples of the epoxy compound (B), the following compounds can be mentioned.

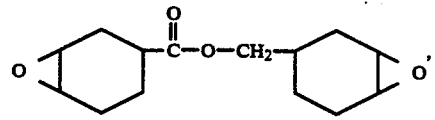

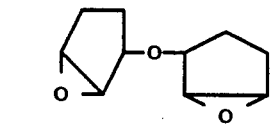

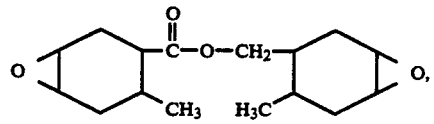

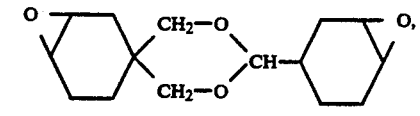

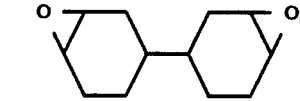

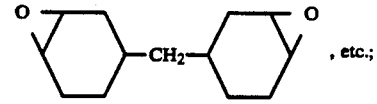

adducts of

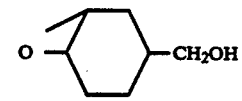

with polyisocyanate compounds (i.e. organic diisocyanates such as aliphatic diisocyanates, e.g. hexamethylene diisocyanate, trimethylhexamethylene diisocyanate, etc., alicyclic diisocyanates, e.g. hydrogenated xylylene diisocyanate, isophorone diisocyanate, etc., and aromatic diisocyanates, e.g tolylene diisocyanate, 4,4'-diphenylmethane diisocyanate, etc., adducts of such organic diisocyanates with polyalcohols, low molecular weight polyesters, water or the like, polymers of said respective organic diisocyanates, and isocyanate biurets, etc.; representative commercial products of these compounds include Burnock D-750, -800, DN-950, -970 and 15-455 (Dainippon Ink and Chemicals Inc.), Desmodur L, NHL, IL and N3390 (Bayer A. G., West Germany), Takenate D-102, -202, -110N and -123N (Takeda Chemical Industries, Ltd.), Coronate L, HL, EH and 203 (Nippon Polyurethane Industry Co., Ltd.) and Duranate 24A-90CX (Asahi Chemical Industry Co., Ltd.); adducts of

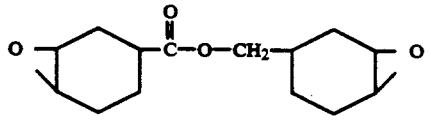

with polybasic acids; the compounds obtainable by oxidizing esters containing unsaturated groups such as

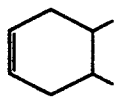

(e.g. esters obtainable by esterifying tetrahydrophthalic anhydride, trimethylolpropane, 1,4-butanediol, etc. and having a number average molecular weight of about 900) with peracetic acid or the like.

Aside from the above compounds containing alicyclic epoxy groups, compounds having non-alicyclic epoxy groups, such as diglycidyl ether, 2-glycidylphenyl glycidyl ether etc., can also be employed.

As the epoxy compound (b), homopolymers of the vinyl monomers represented by the following general formulas (1) through (16) and copolymers thereof with the aforementioned α,β-ethylenically unsaturated monomers (II) can also be employed.

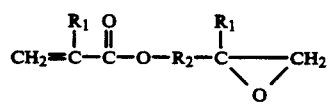 (1)

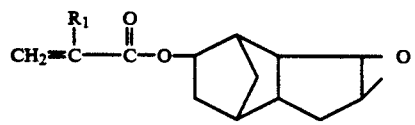 (2)

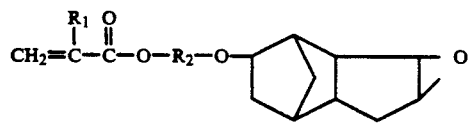 (3)

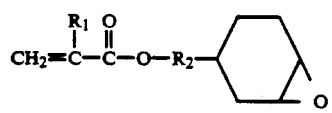 (4)

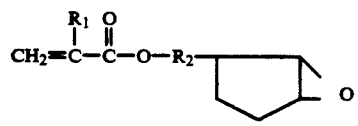 (5)

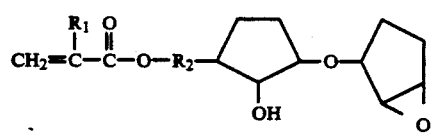 (6)

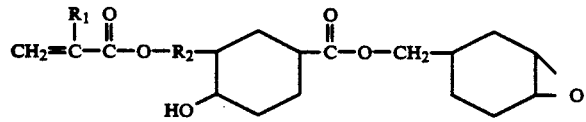 (7)

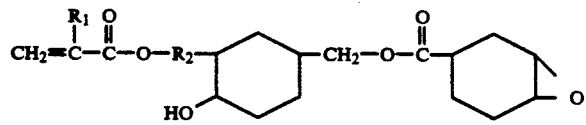 (8)

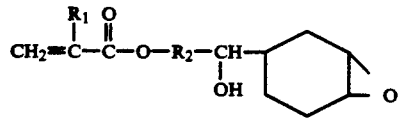 (9)

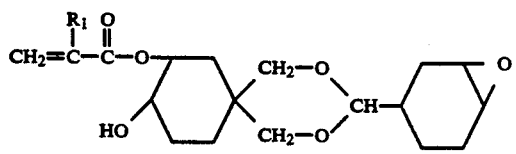 (10)

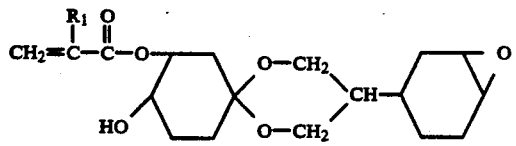 (11)

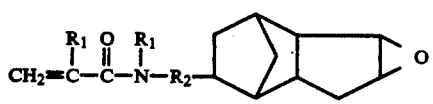 (12)

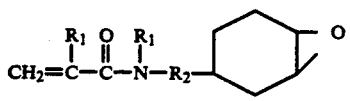 (13)

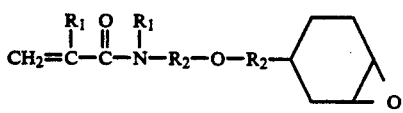 (14)

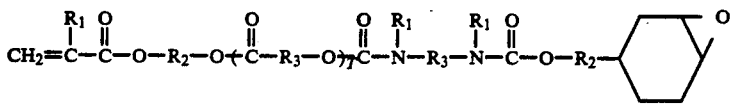 (15)

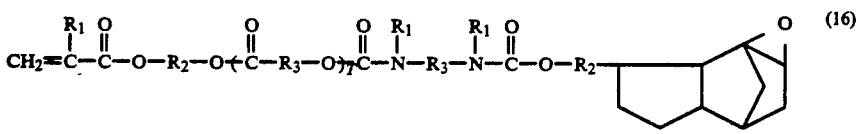 (16)

In the above respective general formulas, $R_1$ means a hydrogen atom or a methyl group; $R_2$ means a divalent aliphatic saturated hydrocarbon group of 1 to 6 carbon atoms; $R_3$ means a divalent hydrocarbon group of 1 to 10 carbon atoms, and T means an integer equal to 0 to 10, inclusive. In the above formulas, the groups $R_1$ are the same or different, and so are the groups $R_2$ and the groups $R_3$.

Among those epoxy group-containing vinyl monomers, the use of alicyclic epoxy group-containing vinyl monomers is preferred from the standpoint of curing property. Thus, when an alicyclic epoxy group-containing vinyl monomer is employed, the addition reaction of the epoxy group to the hydroxyl group proceeds fast and the curing effect is improved.

As examples of the above divalent aliphatic saturated hydrocarbon groups of 1 to 6 carbon atoms, straight-chain or branched alkylene groups such as methylene, ethylene, propylene, tetramethylene, ethylethylene, pentamethylene, hexamethylene, etc. can be mentioned.

As examples of the divalent hydrocarbon group containing 1 to 10 carbon atoms, there may be mentioned methylene, ethylene, propylene, tetramethylene, ethylethylene, pentamethylene, hexamethylene, decamethylene, phenylene,

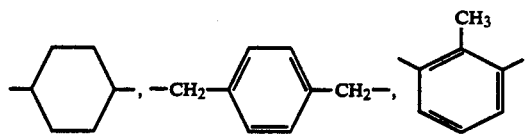

and so on.

As the epoxy compound (B), there may also be employed the compounds obtainable by reacting any of said high molecular weight hydroxy compounds (A) with a compound containing one isocyanate group and one epoxy group per molecule (for example,

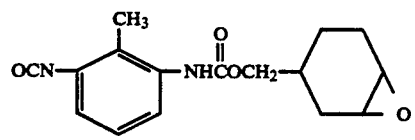

-continued

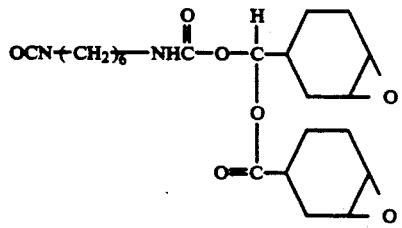

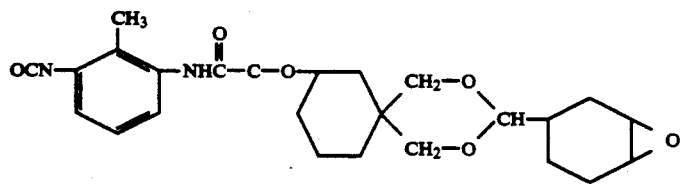

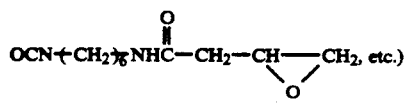

in the proportion of more than one mole of the latter compound to one hydroxyl group in the former compound so as to react all the hydroxyl groups contained in the hydroxy compound (A).

The silane compound (C) is a compound containing an average of one or more functional groups selected from the class consisting of alkoxysilane, silanol and acyloxysilane groups (hereinafter referred to simply as silane groups) per molecule. If the average number of silane groups is less than 1, the curing performance and gel fraction ratio are decreased. On the other hand, if too many silane groups are present, the reaction between silane group and epoxy group predominates to decrease the number of epoxy groups available for reaction with hydroxyl groups to thereby adversely affect the curing performance and gel fraction ratio. Therefore, the number of silane groups in the molecule is preferably not more than 2,500 on the average.

The silane compound (C) should have a number average molecular weight of 104 to 200,000. Silane compounds with number average molecular weights less than 104 are hardly available, while silane compounds with number average molecular weights in excess of 200,000 are not well compatible with other components and fail to give weather-resistant cured films.

As the alkoxy groups in silane compounds (C), alkoxy groups containing 1 to 6 carbon atoms are preferred. Thus, for example, methoxy, ethoxy, n-propoxy, isopropoxy and n-butoxy can be mentioned. As to acyloxy groups, those containing $C_{1-6}$ alkyl groups are preferred. Thus, acetoxy, propioxy, butyroxy, etc. can be mentioned by way of example.

As specific examples of silane compound (C), the following compounds (1) through (7) can be mentioned.

(1) Compounds of general formulas (17) through (20).

$$R_5O-\underset{\underset{R_4}{|}}{\overset{\overset{R_4}{|}}{Si}}-R_4, \quad (17)$$

$$R_5O-\underset{\underset{OR_5}{|}}{\overset{\overset{R_4}{|}}{Si}}-R_4 \quad (18)$$

$$R_5O-\underset{\underset{OR_5}{|}}{\overset{\overset{R_4}{|}}{Si}}-OR_5, \quad (19)$$

$$R_5O-\underset{\underset{OR_5}{|}}{\overset{\overset{OR_5}{|}}{Si}}-OR_5 \quad (20)$$

where all occurrences of $R_4$ may be the same or different and each means a $C_{1-6}$ alkyl group or a phenyl group; all occurrences of $R_5$ may be the same or different and each means a $C_{1-6}$ alkyl group, a hydrogen atom or $$-\overset{\overset{O}{\|}}{C}-R_6$$

where $R_6$ is a $C_{1-6}$ alkyl group.

As examples of said $C_{1-6}$ alkyl group, there may be mentioned methyl, ethyl, n-propyl, iso-propyl, n-butyl, n-pentyl and n-octyl.

As examples of the compound of general formula (17), there may be mentioned trimethylmethoxysilane, trimethylethoxysilane, triethylpropoxysilane, triphenylmethoxysilane, triphenylbutyloxysilane, trimethylsilanol and triphenylsilanol.

As examples of the compound of general formula (18), there may be mentioned dimethyldimethoxysilane, dibutyldimethoxysilane, di-isopropyldipropoxysilane, diphenyldibutoxysilane, diphenyldiethoxysilane, diethyldisilanol, dihexyldisilanol and so on.

As examples of the compound of general formula (19), there may be mentioned methyltrimethoxysilane, methyltriethoxysilane, ethyltriethoxysilane, propyltrimethoxysilane, phenyltriethoxysilane, phenyltributoxysilane, hexyltriacetoxysilane, methyltrisilanol, phenyltrisilanol and so on.

Examples of the compound of general formula (20) include tetramethoxysilane, tetraethoxysilane, tetrapropoxysilane, tetracetoxysilane, diisopropoxydivaleroxysilane, tetrasilanol and so on.

Among these silane compounds, those having number average molecular weights from 104 to 40,000 are preferred and those in the range of 104 to 30,000 are more desirable. Silane compounds with number average molecular weights less than 104 are not readily available, while silane compounds with number average molecular weights exceeding 40,000 are not well compatible with the other components so that the cured film does not have sufficient weather resistance.

(2) Homopolymers of compounds of general formula

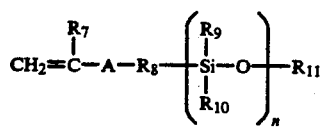
(21)

wherein A means

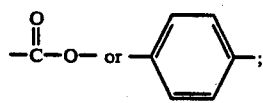

$R_7$ means a hydrogen atom or a methyl group; $R_8$ means a divalent aliphatic saturated hydrocarbon group containing 1 to 6 carbon atoms; $R_9$ and $R_{10}$ may be the same or different and each means a hydroxyl group, a phenyl group, an alkyl group of 1 to 6 carbon atoms, an alkoxy group of 1 to 6 carbon atoms or an acyloxy group; $R_{11}$ means a hydrogen atom or an alkyl group of 1 to 6 carbon atoms; n is an integer equal to 1 through 10, inclusive.

Referring to general formula (21), the divalent aliphatic saturated hydrocarbon group of 1 to 6 carbon atoms, represented by $R_8$, is a straight-chain or branched alkylene group such as methylene, ethylene, propylene, tetramethylene, ethylethylene, pentamethylene, hexamethylene and the like. The alkyl group of 1 to 6 carbon atoms, represented by $R_9$, $R_{10}$ and $R_{11}$, is a straight-chain or branched alkyl group such as methyl, ethyl, n-propyl, isopropyl, n-butyl, isobutyl, sec-butyl, tert-butyl, n-pentyl, isopentyl, neopentyl, n-hexyl, isohexyl and so on. The alkoxy group of 1 to 6 carbon atoms, represented by $R_9$ and $R_{10}$, is a straight-chain or branched alkoxy group such as methoxy, ethoxy, n-propoxy, isopropoxy, n-butoxy, isobutoxy, sec-butoxy, tert-butoxy, n-pentoxy, isopentoxy, n-hexyloxy, isohexyloxy and the like. Referring, further, to general formula (21), where n is not less than 2, all occurrences of $R_9$ and $R_{10}$, respectively, may represent the same group or different groups.

Among the compounds of general formula (21) which are used as monomers in the present invention, those in which A represents

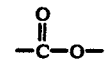

include, among others, γ-(meth)acryloxypropyltrimethoxysilane, γ-(meth)acryloxypropyltriethoxysilane, γ-(meth)acryloxypropyltripropoxysilane, γ-(meth)acryloxypropylmethyldimethoxysilane, γ-(meth)acryloxypropylmethyldiethoxysilane, γ-(meth)acryloxypropylmethyldipropoxysilane, γ-(meth)acryloxybutylphenyldimethoxysilane, γ-(meth)acryloxybutylphenyldiethoxysilane, γ-(meth)acryloxybutylphenyldipropoxysilane, γ-(meth)acryloxypropyldimethylmethoxysilane, γ-(meth)acryloxypropyldimethylethoxysilane, γ-(meth)acryloxypropylphenylmethylmethoxysilane, γ-(meth) acryloxypropylphenylmethylethoxysilane,

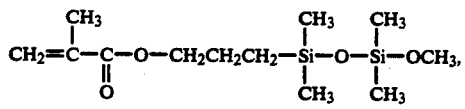

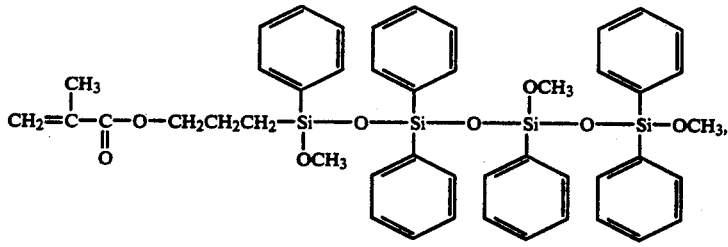

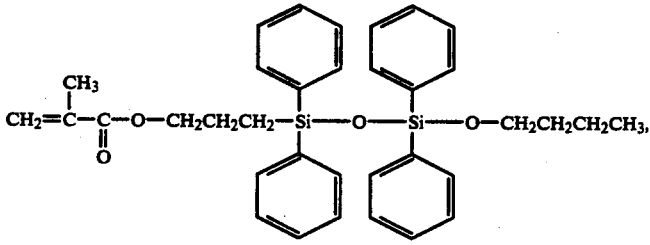

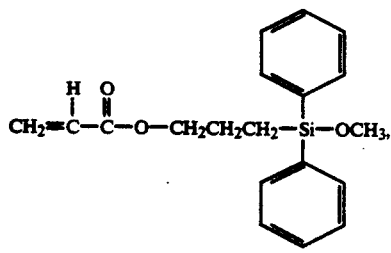
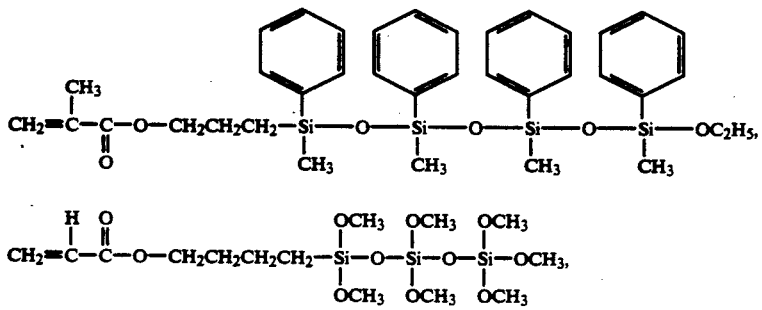
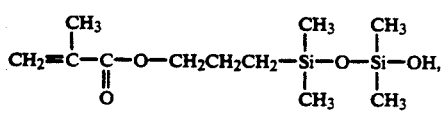
γ-(meth)acryloxypropyltrisilanol, γ-(meth)acryloxypropylmethyldisilanol, γ-(meth)acryloxybutylphenyldisilanol, γ-(meth)acryloxypropyldimethylsilanol, γ-(meth)acryloxypropylphenylmethylsilanol,
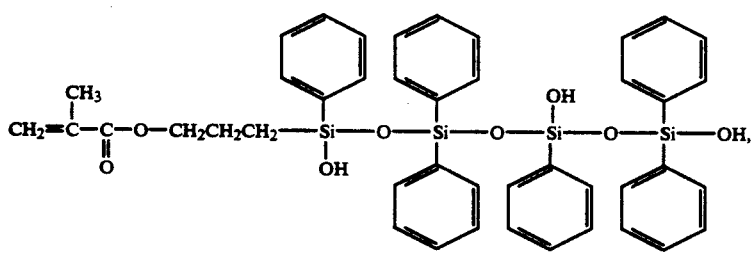
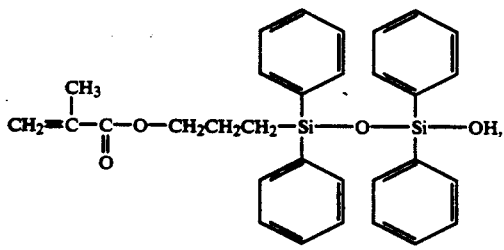
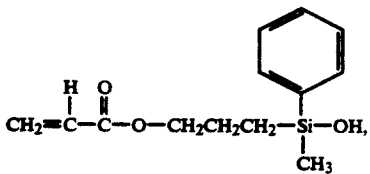

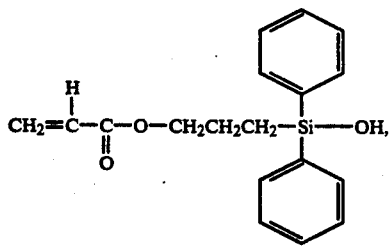
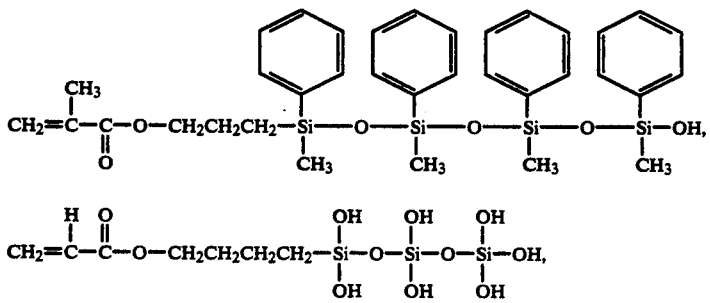
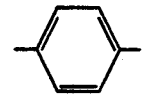
and so on.
Among the compounds of general formula (21), those in which A represents
include, among others,
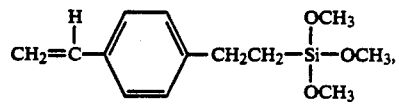
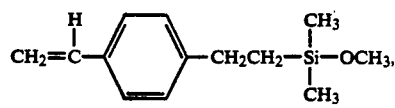
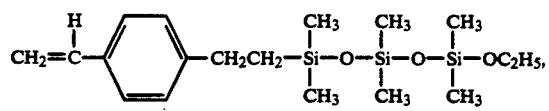
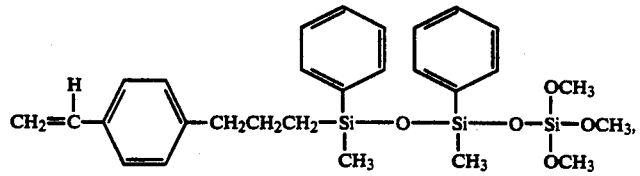
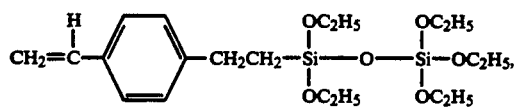
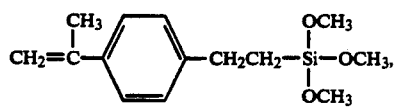

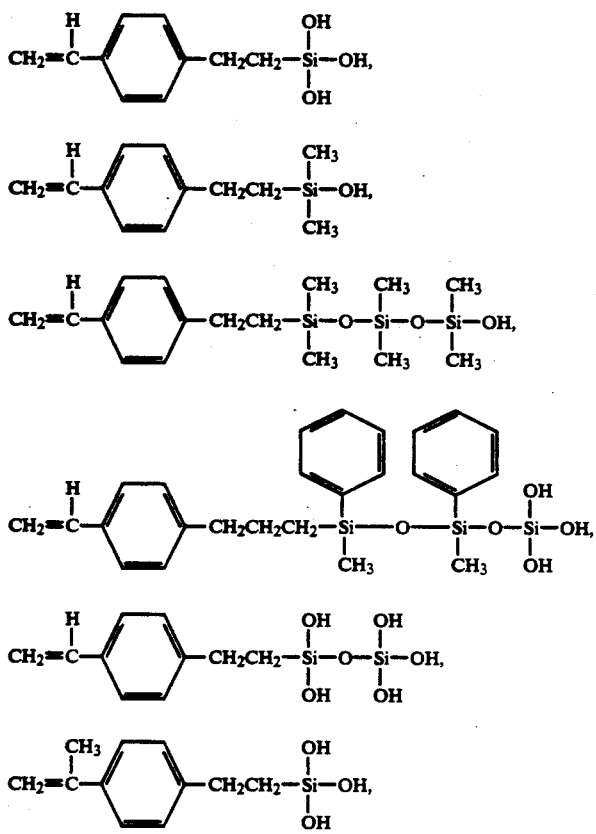

and so on.

(3) Copolymers of compounds of general formula (21) with α,β-ethylenically unsaturated monomers (II)

(4) Homopolymers of polysiloxane macromonomers (for example, the macromonomers described in Japanese Laid-open Patent Application KOKAI No. 275132/1987) which are obtainable by reacting 30 to 0.001 mole percent of a compound of general formula (21) with 70 to 99.999 mole percent of at least one of the compounds of general formulas (17) through (20) and having a number average molecular weight of 400 to 100,000. The number average molecular weights of these homopolymers are preferably in the range of 3,000 to 200,000, more preferably in the range of 5,000 to 80,000.

(5) Copolymers of said polysiloxane macromonomers with α,β-ethylenically unsaturated monomers (II). The number average molecular weights of these copolymers is preferably 3,000 to 200,000, more preferably 5,000 to 80,000.

(6) Compounds obtainable by reacting a compound containing an isocyanato group and either an alkoxysilane group or an acyloxysilane group per molecule (for example,

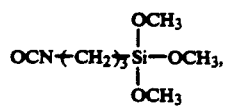

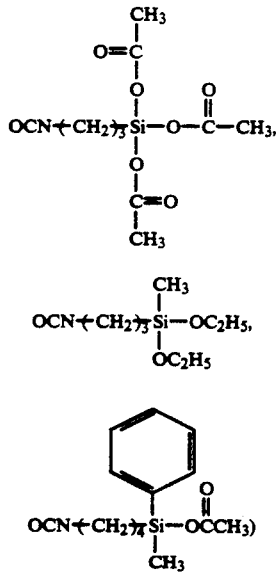

with said hydroxy compounds (A) in the ratio of one mole of the former to one hydroxyl group in the hydroxy compounds (A) so as to react all the hydroxyl groups contained in (A).

(7) Compounds obtainable by reacting said compound containing an isocyanate group and either an alkoxysilane group or an acyloxysilane group per molecule with a polyhydric alcohol, which is used as a starting material for said polyester polyol among said high molecular weight hydroxy compounds (A), in the ratio of one mole of the former to one hydroxyl group in the polyhydric alcohol, to react all the hydroxyl groups contained in the alcohol.

Among the above-mentioned various silane compounds (C), the polymers derived from polysiloxane macromonomers as mentioned above under (4) and (5) are particularly advantageous in that the cured film has a high gel fraction ratio and is superior in acid resistance, impact resistance and other physical properties.

The aforementioned high molecular weight compound (E) containing both epoxy and silane groups, which is employed in Invention II, is a compound containing an average of 2 or more epoxy groups per molecule and an average of 1 or more functional groups selected from the class consisting of alkoxysilane, silanol and acyloxysilane groups (silane groups) per molecule. If the number of epoxy or silane groups is less than the above-mentioned range, the curing performance and gel fraction ratio will be decreased. On the other hand, if the number of silane groups is too many, the epoxy groups are consumed as mentioned above to reduce the number of epoxy groups available for reaction with hydroxyl groups so that the curability of the resin composition is sacrificed. The average number of silane groups per molecule is preferably not more than 2,500. From the standpoint of curability, the number of epoxy groups per molecule need not be more than 500 on the average. The number average molecular weight of high molecular compound (E) is 3,000 to 200,000, preferably 5,000 to 80,000. If the molecular weight is less than 3,000, curing performance and the weather resistance of the cured film will not be as good as desired. On the other hand, if the molecular weight of (E) exceeds 200,000, the compatibility thereof with the other components will not be fully satisfactory. The alkoxy and acyloxy groups in the alkoxysilane and acyloxysilane groups in high molecular weight compound (E) may for example be those mentioned in connection with said silane compound (C).

As examples of high molecular weight compound (E), there may be mentioned the following compounds.

(1) Copolymers obtainable by reacting said compound of general formula (21) or said polysiloxane macromonomer (such as those described in Japanese Laid-open Patent Application KOKAI No. 275132/1987), which is obtainable by reacting a compound of general formula (21) with at least one of the compounds of general formulas (17) through (20) in a ratio of 30 to 0.001 mole percent of the former to 70 to 99.999 mole percent of the latter and having a number average molecular weight of 400 to 100,000, with said epoxy group-containing vinyl monomer of any of general formulas (1) through (16) and, if necessary, further with said $\alpha,\beta$-ethylenically unsaturated monomer (II).

(2) Compounds obtainable by reacting a high molecular weight hydroxy compound (A) containing an average of 3 or more hydroxyl groups per molecule, which can be prepared by adjusting the starting materials in the synthesis of (A), said silane compound (C), which contains both isocyanate and alkoxysilane or acyloxysilane groups in the molecule as mentioned under (7) in the listing of examples of (C), and a epoxy compound (B) containing both isocyanate and epoxy groups in such a manner that the average number of epoxy groups per molecule will be at least 2 and the average number of silane groups per molecule will be at least 1.

(3) Homo- or co-condensates of compounds of general formulas

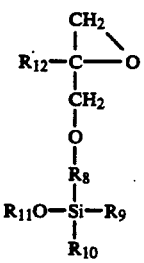

and

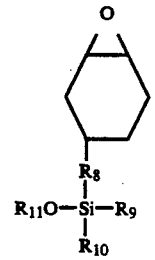

wherein $R_{12}$ means a hydrogen atom or a methyl group; $R_8$, $R_9$, $R_{10}$ and $R_{11}$ have the meanings respectively defined hereinbefore.

As examples of compounds of the above general formulas, there may be mentioned $\gamma$-glycidoxypropyltrimethoxysilane, $\gamma$-glycidoxypropyltriethoxysilane, $\gamma$-glycidoxypropyltriacetoxysilane, glycidoxymethyltrimethoxysilane, $\beta$-glycidoxyethyltriethoxysilane, $\beta$-(3,4-epoxycyclohexyl)ethyltrimethoxysilane, $\beta$-(3,4-epoxycyclohexyl)ethyltriethoxysilane, $\beta$-(3,4-epoxycyclohexyl)ethyltriacetoxysilane, $\gamma$-(3,4-epoxycyclohexyl)propyltriethoxysilane and so on.

Among the above high molecular weight compounds (E), the copolymers obtained by using polysiloxane macromonomers as mentioned under (1) are particularly advantageous in that the resultant film is high in gel fraction ratio, acid resistance and impact resistance.

The high molecular weight compound (F) containing hydroxyl and silane groups, which is employed in Invention III, is a compound containing an average of two or more hydroxyl groups per molecule and an average of at least one functional group selected from the class consisting of alkoxysilane, silanol and acyloxysilane groups (silane groups) per molecule. If the number of hydroxyl or silane groups is less than the above range, curing performance and gel fraction ratio are not as good as desired. From the standpoint of weather resistance and water resistance, the number of hydroxyl groups per molecule is preferably not more than 400. The number of silane groups is preferably not more than 2,500 per molecule from the standpoint of curing performance and gel fraction ratio. The number average molecular weight of high molecular weight compound (F) is 3,000 to 200,000, preferably 5,000 to 80,000. If the molecular weight is less than 3,000, the weather resistance of the cured film will not be fully satisfactory. On the other hand, if the number average molecular weight exceeds 200,000, the compatibility with the other components will not be as good as desired. The alkoxy and acyloxy moieties of the alkoxysilane and acyloxysilane groups contained in high molecular weight compounds (F) may for example be the corresponding groups mentioned for silane compound (C) hereinbefore.

As examples of high molecular compound (F), the following compounds may be mentioned.

(1) Copolymers obtainable by reacting said hydroxyl group-containing vinyl monomer (I) with said compound of general formula (21) and/or said polysiloxane macromonomer (such as those mentioned in Japanese Laid-open Patent Application KOKAI No. 275132/1987) and, if necessary, further with said $\alpha,\beta$-ethylenically unsaturated monomer (II).

(2) Compounds obtainable by reacting a high molecular weight hydroxyl compound (A) containing an average of 3 or more hydroxyl groups per molecule with a compound containing both isocyanate and silane groups in the molecule as mentioned under (7) in the list of examples of silane compound (C) in such a manner that the average number of hydroxyl groups per molecule is at least 2 and the average number of silane groups per molecule is at least 1.

Of the above-mentioned high molecular weight compounds (F), the copolymers prepared using polysiloxane macromonomers as mentioned under (1) are particularly advantageous in that the resulting film is superior in gel fraction ratio, acid resistance, impact resistance and other physical properties.

The low molecular weight epoxy compound (G) is a compound containing an average of 2 or more epoxy groups per molecule. If the average number of epoxy groups per molecule is less than 2, curing performance and gel fraction ratio will not be as good as desired. The number of epoxy groups per molecule is preferably not more than 500 from the standpoint of curability. The number average molecular weight of low molecular weight epoxy compound (G) is 240 to 5,000, preferably 240 to 2,000. Compounds (G) with number average molecular weights less than 240 are not readily available, while compounds with molecular weights over 5,000 are not sufficiently compatible with the other components. As specific examples of low molecular weight epoxy compound (G), the low molecular weight epoxy compounds among the examples of said epoxy group-containing compound (B) can be mentioned.

The high molecular weight compound (H) containing both hydroxyl and epoxy groups, which is employed in Invention IV, is a compound containing an average of 2 or more hydroxyl groups per molecule and an average of 2 or more epoxy groups per molecule. If the number of hydroxyl group or that of epoxy groups is less than the above range, curability will be adversely affected. From the standpoint of weather resistance, water resistance, etc., the number of hydroxyl groups per molecule is preferably not more than 400. From the standpoint of curability, the average number of epoxy groups is preferably not more than 500 per molecule. The number average molecular weight of high molecular weight compound (H) is 3,000 to 200,000, preferably 5,000 to 80,000. If the molecular weight is less than 3,000, weather resistance will not be as high as desired. On the other hand, if the molecular weight exceeds 200,000, the compatibility with the other components will be poor.

As the high molecular weight compound (H), the following compounds can, for example, be employed.
(1) Copolymers obtainable by reacting said hydroxyl group-containing vinyl monomer (I) with any of said epoxy group-containing vinyl monomers of general formulas (1) through (16) and, if necessary, further with said $\alpha,\beta$-ethylenically unsaturated monomer (II) (2) Compounds obtainable by reacting said high molecular weight hydroxy compound (A) containing an average of 3 or more hydroxyl groups per molecule with said epoxy group-containing compound (B) containing both isocyanate and epoxy groups in the molecule in such a manner that the average number of hydroxyl groups per molecule will be at least 2 and the average number of epoxy groups will be at least 2.

The silane compound (C) is the same as the silane compound mentioned for Invention I. Among those silane compounds, copolymers obtained by using polysiloxane macromonomers as described under (4) or (5) in the list of examples of (C) given hereinbefore are particularly advantageous in that not only a high gel fraction ratio but also excellent acid resistance, impact resistance and other physical properties can be obtained.

The components described hereinabove can be respectively provided by the known methods. Thus, the reaction between hydroxyl and isocyanate groups, the condensation reaction of silane groups, copolymerization reaction and other reactions can all be conducted in the known manners. For example, the reaction between isocyanate and hydroxyl groups can be advantageously carried out at a temperature between room temperature and 130° C. over a period of about 30 to 360 minutes. The condensation reaction of silane groups can be carried out in the presence of an acid catalyst (for example, hydrochloric acid, sulfuric acid, formic acid, acetic acid, etc.) at an elevated temperature of about 40° to 150° C. for about 1 to 24 hours. The copolymerization reactions can be carried out under the same conditions as those used generally in the production of acrylic or vinyl resins. In an exemplary synthetic process, the respective monomers are dissolved or dispersed in an organic solvent and in the presence of a radical polymerization initiator, the solution or suspension is heated at a temperature of about 60° to 180° C. with constant stirring. The reaction time generally ranges from about 1 to 10 hours. As the organic solvent, the aforementioned alcohol, ether, ester or hydrocarbon solvent can be selectively employed. A hydrocarbon solvent is preferably used in combination with a different type of solvent from the standpoint of solubility. As the radical initiator, any of usual initiators can be employed. Thus, it may be any of various peroxides such as benzoyl peroxide, t-butyl peroxy-2-ethylhexanoate, etc., and azo compounds such as azobisisobutyronitrile, azobisdimethylvaleronitrile and so on.

As the crosslinking agent, at least one of chelate compounds (D) of aluminum, titanium or zirconium is employed in the present invention. Preferred is a chelate compound containing a compound which shows keto-enol tautomerism as a ligand forming a stable chelate ring.

As examples of said compound which shows keto-enol tautomerism, there may be mentioned $\beta$-diketones (acetylacetone etc.), acetoacetic acid esters (methyl acetoacetate etc.), malonic acid esters (ethyl malonate etc.), ketones having a hydroxyl group in the $\beta$-position (diacetone alcohol etc.), aldehydes having a hydroxyl group in the $\beta$-position (salicylaldehyde etc.), esters having a hydroxyl group in the $\beta$-position (methyl salicylate etc.) and so on. Particularly satisfactory results are obtained when acetoacetic esters and $\beta$-diketones are employed.

The aluminum chelate can be easily prepared by mixing generally one mole equivalent of an aluminum alkoxide of the general formula

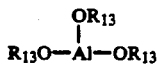

(22)

wherein all occurrences of $R_{13}$ may be the same or different and each means an alkyl group of 1 to 20 carbon atoms or an alkenyl group with about 1 to 3 mole equivalents of a compound which, as aforesaid, shows keto-enol tautomerism, if necessary with heating.

The alkyl group containing 1 to 20 carbon atoms include, in addition to the $C_{1-6}$ alkyl groups mentioned hereinbefore, heptyl, octyl, nonyl, decyl, undecyl, dodecyl, tridecyl, tetradecyl, octadecyl and so on. As examples of said alkenyl group, there may be mentioned vinyl, allyl and so on.

As examples of the aluminum alkoxide of general formula (22), there may be mentioned aluminum trimethoxide, aluminum triethoxide, aluminum tri-n-propoxide, aluminum triisopropoxide, aluminum tri-n-butoxide, aluminum triisobutoxide, aluminum tri-sec-butoxide, aluminum tri-tert-butoxide and so on. Particularly preferred are aluminum triisopropoxide, aluminum tri-sec-butoxide and aluminum tri-n-butoxide.

The titanium chelate can be prepared, for example by mixing generally one mole equivalent, as titanium, of a titanate compound of the general formula

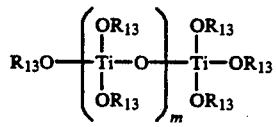

(23)

wherein m represents an integer equal to 0 through 10, inclusive, and $R_{13}$ has the same meaning as defined hereinbefore, with about 1 to 4 mole equivalents of a compound which, as aforesaid, shows keto-enol tautomerism, if necessary with heating.

As examples of the titanate of general formula (23) wherein m is equal to 0, there may be mentioned, among others, tetramethyl titanate, tetraethyl titanate, tetra-n-propyl titanate, tetraisopropyl titanate, tetra-n-butyl titanate, tetraisobutyl titanate, tetratert-butyl titanate, tetra-n-pentyl titanate, tetra-n-hexyl titanate, tetraisooctyl titanate, tetra-n-lauryl titanate and so on. Particularly useful are tetraisopropyl titanate, tetra-n-butyl titanate, tetraisobutyl titanate and tetra-tert-butyl titanate. As to the titanate of general formula (23) wherein m is 1 or more, the dimers to undecamers (m =1 to 10) of tetraisopropyl titanate, tetra-n-butyl titanate, tetraisobutyl titanate or tetra-tert-butyl titanate are preferred.

The zirconium chelate can be prepared, for example by mixing generally one mole equivalent, as zirconium, of a zirconate compound of the general formula:

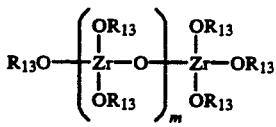

(24)

wherein m and $R_{13}$ are as defined hereinbefore, with about 1 to 4 mole equivalents of said compound which shows keto-enol tautomerism, if necessary with heating.

As examples of the zirconate of general formula (24) wherein m is equal to 0, there may be mentioned tetraethyl zirconate, tetra-n-propyl zirconate, tetraisopropyl zirconate, tetraisobutyl zirconate, tetra-n-butyl zirconate, tetra-sec-butyl zirconate, tetra-tert-butyl zirconate, tetra-n-pentyl zirconate, tetra-tert-pentyl zirconate, tetra-tert-hexyl zirconate, tetra-n-heptyl zirconate, tetra-n-octyl zirconate, tetra-n-stearyl zirconate and so on. Particularly preferred are tetraisopropyl zirconate, tetra-n-propyl zirconate, tetraisobutyl zirconate, tetra-n-butyl zirconate, tetra-sec-butyl zirconate and tetra-tert-butyl zirconate. As to the zirconate of general formula (24) wherein m is equal to 1 or more, the dimers to undecamers (m=1 to 10) of tetraisopropyl zirconate, tetra-n-propyl zirconate, tetra-n-butyl zirconate, tetraisobutyl zirconate, tetra-sec-butyl zirconate or tetra-tert-butyl zirconate are preferred. The zirconium chelate compound may contain an association of such zirconates as a constituent unit.

Among preferred chelate compounds for purposes of this invention are such aluminum chelate compounds as tris(ethylacetoacetate)aluminum, tris(n-propylacetoacetate)aluminum, tris(isopropylacetoacetate)aluminum, tris(n-butylacetoacetate)aluminum, isopropoxybis(ethylacetoacetate)aluminum, diisopropoxyethylacetoacetatealuminum, tris(acetylacetonato)aluminum, tris(propionylacetonato)aluminum, diisopropoxypropionylacetonatoaluminum, acetylacetonatobis(propionylacetonato)aluminum, monoethylacetoacetatebis(acetylacetonato)aluminum, monoacetylacetonatobis(ethylacetoacetate)aluminum, etc., such titanium chelate compounds as diisopropoxybis(ethylacetoacetate)titanium, diisopropoxybis(acetylacetonato)titanium, etc., and such zirconium chelate compounds as tetrakis(acetylacetonato)zirconium, tetrakis(n-propylacetoacetate)zirconium, tetrakis(ethylacetoacetate)zirconium and so on.

If, in the practice of this invention, unchelated alkoxy compounds of aluminum, titanium or zirconium of general formulas (22) through (24), are used as cross-linking agents, the pot life is shortened so that the resulting composition cannot be used as a one-package composition.

As the chelate compound to be used as a crosslinking agent in the present invention, the above-mentioned respective chelate compounds of aluminum, zirconium and titanium can be used either singly or in combination.

In the resin composition of Invention I, the proportions of high molecular weight hydroxy compound (A) and epoxy compound (B) are 5 to 95 weight percent, preferably 20 to 80 weight percent, for the former and 95 to 5 weight percent, preferably 80 to 20 weight percent, for the latter, both based on the combined weight of (A) and (B). If the ratio of the two compounds are outside the above range, low-temperature curability will not be as good as desired. Based on 100 weight parts of high molecular weight hydroxy compound (A) and epoxy compound (b) combined, the silane compound (C) is used in a proportion of 0.1 to 50 parts by weight, preferably 1 to 20 parts by weight. If the proportion of silane compound (C) is less than 0.1 part by weight, curing performance will be adversely affected. On the other hand, use of (C) in excess of 50 parts by weight is also disadvantageous in that the solvent resistance of the film will be adversely affected by the residue of silane compound (C). The metal chelate compound (D) is used in a proportion of 0.01 to 10 parts by weight, preferably 0.1 to 5 parts by weight, based on 100 parts by weight of high molecular weight hydroxy compound (A) and epoxy compound (B) combined. If the proportion of metal chelate compound (D) is less than 0.01 part by weight, curing performance will be adversely affected, while the use of (D) in excess of 10 parts by weight will result in reduced water resistance of the cured film.

In the resin composition of Invention II, the proportion of high molecular weight hydroxy compound (A) is 5 to 95 weight percent, preferably 20 to 80 weight percent and that of high molecular weight compound containing both epoxy and silane groups (E) is 95 to 5 weight percent, preferably 80 to 20 weight percent, both based on the combined amount of (A) and (E). If the ratio of the two components is outside the above range, the curing performance, particularly low-temperature curability, of the composition will not be as good as desired. The metal chelate compound (D) is used in a proportion of 0.01 to 10 parts by weight, preferably 0.1 to 5 parts by weight based on 100 parts by weight of said high molecular weight hydroxy compound (A) and high molecular weight compound containing both epoxy and silane groups (E) combined. If the proportion of metal chelate compound (D) is less than 0.01 part by weight, the curability of the composition will not be as good as desired, while the use of (D) in excess of 10 parts by weight will result in reduced water resistance of the cured film.

In the resin composition of Invention III, said high molecular weight compound containing both hydroxyl and silane groups (F) is used in a proportion of 5 to 95 weight percent, preferably 20 to 80 weight percent and said lower molecular weight epoxy compound (G) in a proportion of 95 to 5 weight percent, preferably 80 to 20 weight percent based on the combined weight of (F) and (G). If the ratio of the two compounds is outside the above range, the curing performance, particularly low-temperature curability, of the composition will not be fully satisfactory. The metal chelate compound (D) is used in a proportion of 0.01 to 10 parts by weight, preferably 0.1 to 5 parts by weight based on 100 parts by weight of said high molecular weight compound containing both hydroxyl and silane groups (F) and low molecular weight epoxy compound (G) combined. If the proportion of metal chelate compound (D) is less than 0.01 part by weight, curing performance will not be satisfactory, while the use of (D) in excess of 10 parts by weight will detract from the water resistance of the film.

In the resin composition of Invention IV, said high molecular weight compound containing both hydroxyl and epoxy groups (H) is used in a proportion of 5 to 95 weight percent, preferably 20 to 80 weight percent and said silane compound (C) in a proportion of 95 to 5 weight percent, preferably 80 to 20 weight percent based on the combined weight of (H) and (C). If the ratio of the two compounds is outside the above range, the curing performance, particularly low-temperature curability, of the composition will not be as good as desired. The metal chelate compound (D) is used in a proportion of 0.01 to 10 parts by weight, preferably 0.1 to 5 parts by weight based on 100 parts by weight of said high molecular weight compound containing both hydroxyl and epoxy groups (H) and silane compound (C) combined. If the proportion of metal chelate compound (D) is less than 0.01 part by weight, curability will not be as good as desired, while the incorporation of (D) in excess of 10 parts by weight will result in reduced water resistance of the cured film.

If necessary, inorganic and organic pigments may be incorporated in the resin compositions of the present invention. As examples of the inorganic pigment, there may be mentioned oxide pigments (such as titanium dioxide, red iron oxide, chromium oxide, etc., hydroxide pigments (such as alumina white etc.), sulfate pigments (such as precipitated barium sulfate, clay etc.), carbonate pigments (such as precipitated calcium carbonate etc.), carbon pigments (such as carbon black etc.), and various metal powders (such as aluminum powder, bronze powder, zinc dust, etc.). As examples of said organic pigments, azo colors (such as lake red, fast yellow, etc.) and phthalocyanine colors (such as phthalocyanine blue etc.) can be mentioned.

If necessary, the resin compositions of the present invention can be used as dissolved in organic solvents.

From the standpoint of curing rate of the resin composition, an organic solvent having a boiling point not exceeding about 150° is preferred, although this is not an essential requirement. Preferred organic solvents include hydrocarbon solvents such as toluene, xylene, etc., ketone solvents such as methyl ethyl ketone, methyl isobutyl ketone, etc., ester solvents such as ethyl acetate, butyl acetate, etc., ether solvents such as dioxane, ethylene glycol diethyl ether, etc., and alcohol solvents such as butanol, propanol and so on. While these solvents may be used alone or in suitable combination, alcohol solvents are preferably used in combination with other kinds of solvents from the standpoint of solubility of the resin. While the resin concentration varies with different applications, it is generally about 10 to 70 weight percent.

The resin compositions of the present invention can be used with advantage in such applications as coatings, adhesives, inks and so on.

When any of the resin compositions of the present invention is to be used as a coating material, it can be applied by any routine coating method, such as spray coating, roll coating or brush coating.

The resin compositions of the present invention can be easily cured at a low temperature not exceeding 100° C. and even at room temperature without heating. In the latter case, complete cure can be achieved generally in about 8 hours to about 7 days. When the curing reaction is conducted at an elevated temperature of about 40° to 100° C., complete cure occurs in as short as about 5 minutes to about 3 hours.

The reason why the resin compositions of the present invention have excellent low-temperature curability seems to be as follows. In the first place, the metal chelate compound reacts with the silane group to give the following bond.

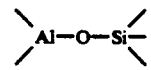

Then, this bond is coordinated to the silanol group (the alkoxysilane and acyloxysilane groups are converted to silanol group by humidity in the atmosphere) to polarize the silanol group as follows.

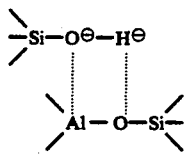

This polarized silanol group reacts with the epoxy group to give the bond:

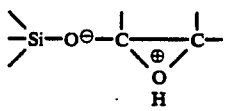

The epoxy group then reacts with a hydroxyl group to give:

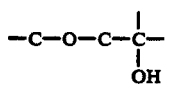

This reaction between the epoxy and hydroxyl groups proceeds at a comparatively low temperature.

Since the compositions of the present invention contain a hydroxyl group-containing compound as an essential component and, in addition, contains epoxy and silane groups and, further, a metal chelate compound, the above reaction appears to proceed very rapidly to insure excellent low-temperature curability.

The resin compositions of the present invention can be implemented by using the respective components in rather liberal proportions. Therefore, the cured product tailored to the intended use can be obtained by mixing the components in suitable proportions before application. By way of illustration, Invention I may be implemented, for example, by a process in which said high molecular weight hydroxy compound (A) as a main component is cured with said epoxy compound (B), silane compound (C) and metal chelate compound (D), a process in which said epoxy compound (B) as a main component is cured with said high molecular weight hydroxy compound (A), silane compound (C) and metal chelate compound (D), or a process in which said silane compound (C) as a main component is cured with said hydroxy compound (A), epoxy compound (B) and metal chelate compound (D).

If a pigment, such as titanium white, is dispersed using a resin containing epoxy, hydroxyl and silanol groups, the silanol groups contained in the resin will react with $Al_2O_3$, $SiO_2$ and $ZnO$, inclusive of their hydrates, on the surface of the pigment (titanium white) to increase the thickness of the resin system or give rise to coarse particles and the metal chelate compound is also liable to react with such metal oxides and hydrates on the surface of titanium white to increase the viscosity of the system. On the other hand, in the resin compositions of the present invention, the above problem can be obviated by dispersing the pigment titanium white using said high molecular weight hydroxy compound (A).

The resin compositions of the present invention insure the following advantageous effects.

1. A highly weather-resistant film can be obtained.

2. Since the curing component can be easily modified, various films tailored to intended uses can be obtained.

3. The curing reaction proceeds smoothly at low temperatures not exceeding about 100° C.

4. The composition has a long pot life and can be used as a one-package coating.

5. The cured film has excellent acid resistance.

The following examples are further illustrative of the present invention.

PRODUCTION EXAMPLE

1. Production of compound (a)

| | |
|---|---|
| $CH_2=C(CH_3)-C(O)-O-CH_2-\text{(epoxycyclohexyl)}$ | 200 g |
| γ-Methacryloxypropyltrimethoxysilane | 100 g |
| n-Butyl acrylate | 700 g |
| Azobisisobutyronitrile | 10 g |

The above starting materials were blended and the mixture was added dropwise to 1,000 g of xylene at a temperature of 110° C. to give an acrylic resin with a number average molecular weight of 30,000 (the average number of epoxy groups per molecule=30 and that of alkoxysilane groups=12).

2. Production of compound (b)

| | |
|---|---|
| Methyltrimethoxysilane | 2720 g |
| γ-Methacryloxypropyltrimethoxysilane | 256 g |
| Deionized water | 1134 g |
| 30% Hydrochloric acid | 2 g |
| Hydroquinone | 1 g |

The above mixture was reacted at 80° C. for 5 hours. The resulting polysiloxane macromonomer had a number average molecular weight of 2,000 and contained one vinyl group (polymerizable unsaturated bond) and 4 hydroxyl groups on the average per mol.

| | |
|---|---|
| The above macromonomer | 300 g (nonvolatile matter) |
| Styrene | 100 g |
| Glycidyl methacrylate | 100 g |
| n-Butyl acrylate | 500 g |
| Azobisisobutyronitrile | 20 g |

The above mixture was added dropwise to 1,000 g of xylene and polymerized at 120° C. to give a clear copolymer. The above copolymer contained an average of 12 silanol groups and an average of 14 glycidyl groups per molecule and had a number average molecular weight of about 20,000.

3. Production of compound (c)

| | |
|---|---|
| Trimethylolpropane | 268 g |
| 1,6-Hexanediol | 118 g |
| Phthalic anhydride | 422 g |

The above mixture was subjected to co-condensation under heating and dehydration to give a polyester polyol.

To 500 g of the above polyester polyol were added 306 g of

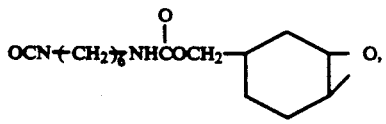

53 g. of OCN†CH₂⁊₃Si(OCH₃)₃ and 0.17 g of dibutyltin laurate and the reaction was conducted at 80° C. for 3 hours. The procedure gave a compound containing an average of 5.5 epoxy groups per molecule and an average of 1.4 alkoxysilane groups per molecule.

4. Production of compound (d)

| | 520 g |
|---|---|
| [structure: epoxycyclohexyl-(CH₂)₃Si(OCH₃)₃] | |
| Deionized water | 54 g |
| Ethanol | 574 g |
| 1N-Hydrochloric acid | 1.5 g |

The above mixture was reacted at 50° C. for 6 hours to give an oligocondensate of silane monomer containing an average of 18 alkoxysilane groups and an average of 14 epoxy groups per molecule.

Production of compound (e)

| [structure: CH₂=CH—C(O)—OCH₂CH₂OC(O)NH†CH₂⁊₆NHC(O)OCH₂-epoxycyclohexyl] | 600 g |
|---|---|
| n-Butyl methacrylate | 400 g |
| Azobisisobutyronitrile | 10 g |

The above mixture was added dropwise to 1,000 g of xylene at 100° C. for polymerization. The procedure gave a compound containing an average of 51 epoxy groups per molecule and having a number average molecular weight of 35,000.

6. Production of compound (f)

| 2-Hydroxyethyl acrylate | 116 g |
|---|---|
| [structure: CH₂=C(CH₃)—C(O)—O—CH₂-epoxycyclohexyl] | 196 g |
| 2-Ethylhexyl methacrylate | 688 g |
| Azobisisobutyronitrile | 10 g |

The above mixture was added dropwise to 1,000 g of xylene at 100° C. for polymerization. The procedure gave a compound having a number average molecular weight of 30,000.

This compound contained an average of 30 epoxy groups and an average of 30 hydroxyl groups per molecule.

7. Production of compound (g)

A mixture of 300 g (nonvolatile matter) of the polysiloxane macromonomer prepared in the production of compound (b), 100 g of styrene, 600 g of n-butyl acrylate and 20 g of azobisisobutyronitrile was added dropwise to 1,000 g of xylene at 120° C. for polymerization. The procedure gave a clear copolymer. This copolymer contained an average of 12 silanol groups per molecule and had a number average molecular weight of about 20,000.

EXAMPLE 1

A resin composition was provided by mixing 100 g of an acrylic polyol (2-hydroxyethyl acrylate/n-butyl methacrylate/styrene/azobisisobutyronitrile = 116 g/734 g/150 g/10 g) containing an average of 30 hydroxyl groups per molecule and having a number average molecular weight of 30,000 with

| [structure: epoxycyclohexyl—C(O)—OCH₂—epoxycyclohexyl] | 20 g |
|---|---|
| Triphenylsilanol | 1 g |
| tris(Acetylacetonato)aluminum | 0.5 g. |

EXAMPLE 2

A resin composition was provided by mixing 100 g of the same acrylic polyol as used in Example 1 with 30 g (nonvolatile matter) of the copolymer prepared in the production of compound (g), 20 g of

[structure: epoxycyclohexyl—C(O)—OCH₂—epoxycyclohexyl]

and 0.5 g. of tris(acetylacetonato)aluminum.

EXAMPLE 3

A resin composition was provided by mixing 100 g of a polyester polyol (phthalic anhydride/neopentyl glycol/trimethylolpropane = 550 g/211 g/239 g) containing an average of 18 hydroxyl groups per molecule and having a number average molecular weight of 10,000 with 100 g (nonvolatile matter) of compound (a) and 1 g of diisopropoxybis(ethylacetoacetate)titanium.

EXAMPLE 4

A resin composition was provided by mixing 166 g of Lumiflon LF-200 (trademark of Asahi Glass Co., Ltd., with an average of 18.5 hydroxyl groups per molecule and a number average molecular weight of 20,000) (nonvolatile matter 60 wt.%) with 80 g (nonvolatile matter) of compound (b) and 0.5 g of tetrakis(ethylacetoacetate)zirconium.

EXAMPLE 5

A resin composition was provided by mixing 100 g of an acrylic polyol (2-hydroxyethyl methacrylate/n-butyl acrylate/methyl methacrylate/azobisiso-butyronitrile=650 g/175 g/175 g/10 g) containing an average of 150 hydroxyl groups per molecule and having a number average molecular weight of 30,000 with 900 g (nonvolatile matter) of compound (c) and 1.8 g of tris(ethylacetoacetate)aluminum.

EXAMPLE 6

A resin composition was provided by mixing 100 g of the same acrylic polyol as used in Example 1 with 30 g (nonvolatile matter) of compound (d) and 1.2 g of tetrakis(n-propylacetoacetate)zirconium.

EXAMPLE 7

| 2-Hydroxyethyl acrylate | 120 g |
| γ-Methacryloxypropyltrimethoxysilane | 20 g |
| n-Butyl methacrylate | 860 g |
| Azobisisobutyronitrile | 5 g |

The above mixture was added dropwise to 1,000 g of a 50:50 (w/w) mixture of xylene and n-butanol at 100° C. for polymerization. The procedure gave a high molecular weight compound containing an average of 46 hydroxyl groups and an average of 11 alkoxysilane groups per molecule and having a number average molecular weight of 45,000. A resin composition was provided by mixing 200 g of the above reaction product with 40 g (nonvolatile matter) of compound (e) and 1.2 g of tris(acetylacetonato)aluminum.

EXAMPLE 8

| 2-Hydroxyethyl acrylate | 120 g |
| Polysiloxane macromonomer, prepared in production of compound (b) | 130 g (nonvolatile matter) |
| n-Butyl methacrylate | 750 g |
| Azobisisobutyronitrile | 5 g |

The above mixture was added dropwise to 1,000 g of a 50:50 (w/w) mixture of xylene and n-butanol at 100° C. for polymerization. The procedure gave a high molecular weight compound containing an average of 46 hydroxyl groups and an average of 12 silanol groups per molecule and having a number average molecular weight of 48,000. A resin composition was provided by mixing 200 g of the above reaction product with 40 g (nonvolatile matter) of compound (e) and 1.2 g of tris(acetylacetonato)aluminum.

EXAMPLE 9

A resin composition was provided by mixing 50 g (nonvolatile matter) of compound (g) with 100 g (nonvolatile matter) of compound (f) and 1.0 g of tetrakis(ethylacetoacetate)zirconium.

EXAMPLE 10

To 100 g of the same acrylic polyol as used in Example 1 was added 500 g of titanium white CR-93 (trademark of Ishihara Sangyo Co., Ltd., titanium dioxide) and the mixture was dispersed on a shaker. To this dispersion were added 800 g (nonvolatile matter) of compound (a) and 5 g of tris-(acetylacetonato)aluminum. The resultant composition was a satisfactory dispersion with a particle size of 5 μm (determined in accordance with ASTM D 1201-64).

COMPARATIVE EXAMPLE 1

A resin composition was provided by adding 30 g of Cymel 303 (trademark of American Cyanamid Company, a methoxysilane resin) to 100 g of the same polyester polyol as used in Example 3.

COMPARATIVE EXAMPLE 2

A resin composition was provided by adding 20 g of Burnock DN-990 (trademark of Dainippon Ink and Chemicals Co., Ltd., a diisocyanate compound; 90 wt. %) to 100 g of the same polyester polyol as used in Example 3.

Film Performance Tests

Each of the resin compositions prepared in Examples 1 through 10 and Comparative Examples 1 and 2 was coated in a dry thickness of 100 μm (provided, however, that a thickness of 50 μm was used for water resistance test and weatherability test) and cured at 80° C. for 10 minutes, and the cured film was subjected to various tests.

Gel fraction ratio: The dry film was peeled off from the glass substrate and extracted with refluxing acetone in a Soxhlet extractor for 6 hours. The gel fraction ratio was expressed in % residue of the film. Impact resistance: Mild steel sheet was used as the substrate. Using a DuPont impact tester, a weight of 500 g (impact core diameter of ½ inch) was dropped on the coated surface and the maximum dropping distance (cm) which did not cause cracking or exfoliation of the coat was determined.

Water resistance: Mild steel sheet was used as the substrate. The testpiece was immersed in lukewarm water (40° C.) for 60 days to check for abnormalities (blisters, whitening, loss of gloss) in the film. Weatherability: Aluminum sheet was used as the substrate. Using the QUV weather-o-meter (The Q-Panel Co., Ltd.; a fluorescent lamp No. QFS-40, UV-B, a wavelength range of 320-280 nm), an irradiation (60° C., 8 hours)-condensation (50° C., 4 hours) cycle was repeated for 2000 hours and the degree of film degradation was grossly evaluated.

Acid resistance: Glass plate was used as the substrate. The testpiece was immersed in 40% aqueous $H_2SO_4$ (40° and 60° C.) for 5 hours and the appearance (gloss, whitening) of the coated surface was grossly evaluated. Coated surface condition: Mild steel sheet was used as the substrate. The film was checked for loss of gloss, shrinkage, cracks, exfoliation, pigment grains.

Pot life: Each composition was allowed to stand in an open vessel in an environment of 20° C. and 70% R.H. and the time period during which no viscosity increase took place was determined.

The results of the above tests are shown in Table 1.

TABLE 1

|  | Examples | | | | | | | | | | Comparative Examples | |
| --- | --- | --- | --- | --- | --- | --- | --- | --- | --- | --- | --- | --- |
|  | 1 | 2 | 3 | 4 | 5 | 6 | 7 | 8 | 9 | 10 | 1 | 2 |
| Gel fraction ratio | 90.3 | 94.6 | 90.2 | 98.5 | 94.2 | 98.0 | 95.9 | 98.9 | 97.0 | 90.5 | 76.0 | 96.8 |
| Impact resistance | 40 | 50< | 40 | 50< | 40 | 50 | 50 | 50< | 50< | 40 | 40 | 50 |
| Water resistance | Good | Good | Good | Good | Good | Good | Good | Good | Good | Good | Poor | Good |
| Weather-ability | Good | Good | Good | Good | Good | Good | Good | Good | Good | Good | Poor | Poor |
| Acid resistance 40° C. | Good | Good | Good | Good | Good | Good | Good | Good | Good | Good | Marked decrease in gloss | Good |
| Acid resistance 60° C. | Slight decrease in gloss | Good | Slight decrease in gloss | Good | Slight decrease in gloss | Very slight decrease in gloss | Slight decrease in gloss | Good | Good | Slight decrease in gloss | Marked decrease in gloss | Decrease in gloss |
| Coated surface condition | Good | Good | Good | Good | Good | Good | Good | Good | Good | Good | Good | Good |
| Pot life | 150< | 150< | 150< | 150< | 150< | 150< | 150< | 150< | 150< | 150< | 150< | 10< |

What is claimed is:

1. A resin composition comprising a first high molecular weight compound having a number average molecular weight of 3,000 to 2,000 and having an average of 2 or more hydroxyl groups per molecule as its reactant groups, a second high molecular weight compound having a number average molecular weight of 3,000 to 200,000 and having an average of 2 or more epoxy groups and an average of 1 or more functional groups selected from the groups consisting of alkoxysilane, silanol and acyloxysilane groups as its reactant groups, wherein the first and second high molecular weight compounds are different, and at least one metal chelate compound selected from the group consisting of aluminum chelate compounds, titanium chelate compounds and zirconium chelate compounds, said composition containing 5 to 95 weight percent of said first high molecular weight compound, 95 to 5 weight percent of said second high molecular weight compound, and 0.01 to 10 parts by weight of said metal chelate compound, based on the combined weights of said first and second high molecular weight compounds.

2. A resin composition according to claim 1, wherein said first high molecular weight compound has an average of 2 to 400 hydroxyl groups per molecule and said second high molecular weight compound has an average of 2 to 500 epoxy groups and a average of 1 to 2500 said functional groups per molecule.

* * * * *